United States Patent [19]

Kalasek

[11] 4,195,061
[45] Mar. 25, 1980

[54] STERILIZATION APPARATUS FOR INFUSION SOLUTIONS OR THE LIKE, FILLED IN CONTAINERS

[75] Inventor: Karl Kalasek, Vienna III, Austria

[73] Assignee: Firma Vereinigte Edelstahlwerke Aktiengesellschaft, Vienna I, Austria

[21] Appl. No.: 906,579

[22] Filed: May 16, 1978

[30] Foreign Application Priority Data

May 17, 1977 [AT] Austria .................. 3532/77

[51] Int. Cl.² .................. A61L 1/00; A61L 3/00
[52] U.S. Cl. .................. 422/109; 422/25; 422/26; 422/108; 422/110; 422/111; 422/116; 422/297; 422/302
[58] Field of Search .................. 422/25, 26, 108, 109, 422/110, 111, 116, 297, 302

[56] References Cited

U.S. PATENT DOCUMENTS

| 2,868,616 | 1/1959 | Poitras | 422/25 |
|---|---|---|---|
| 2,870,024 | 1/1959 | McK.Martin | 422/302 X |
| 3,088,180 | 5/1963 | Lauterbach | 422/25 |
| 3,366,442 | 1/1968 | Neiss | 422/25 X |
| 3,531,300 | 9/1970 | Greenberg et al. | 422/25 X |
| 3,619,126 | 11/1971 | Carvallo | 422/25 |
| 3,861,872 | 1/1975 | MacFarlane | 422/25 |
| 3,897,818 | 8/1975 | Champel | 422/25 X |
| 3,917,450 | 11/1975 | Martensson et al. | 422/297 X |
| 4,088,444 | 5/1978 | Byrne | 422/25 |

FOREIGN PATENT DOCUMENTS 132909  9/1951  Sweden .................. 422/304

Primary Examiner—Barry S. Richman
Attorney, Agent, or Firm—Ernest F. Marmorek

[57] ABSTRACT

A sterilization device for processing a plurality of containers disposed on support devices therefor, includes a housing provided with a passage for receiving and discharging a succession of the support devices, a preheating arrangement for preheating the containers to a first predetermined temperature within the housing, a heating arrangement for heating the containers to a predetermined sterilization temperature within the housing upon the containers having been heated to the predetermined temperature, and a cooling mechanism for cooling the containers to a second predetermined temperature following sterilization of the containers by the heating arrangement.

13 Claims, 5 Drawing Figures

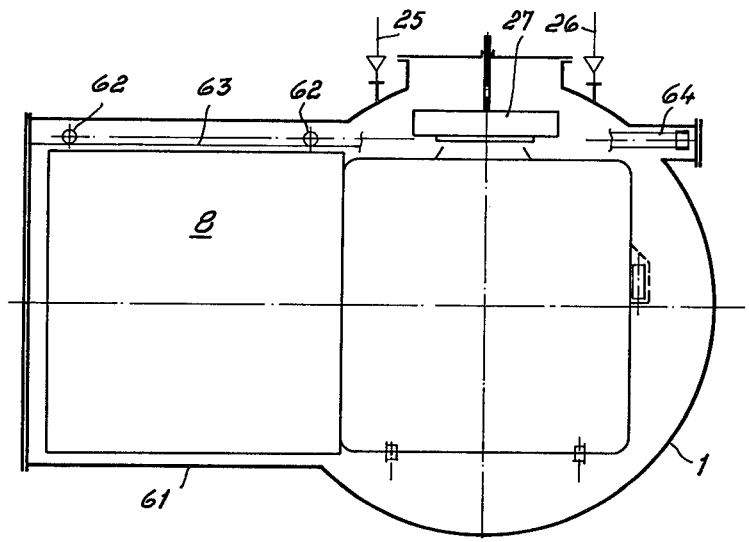
FIG. 2
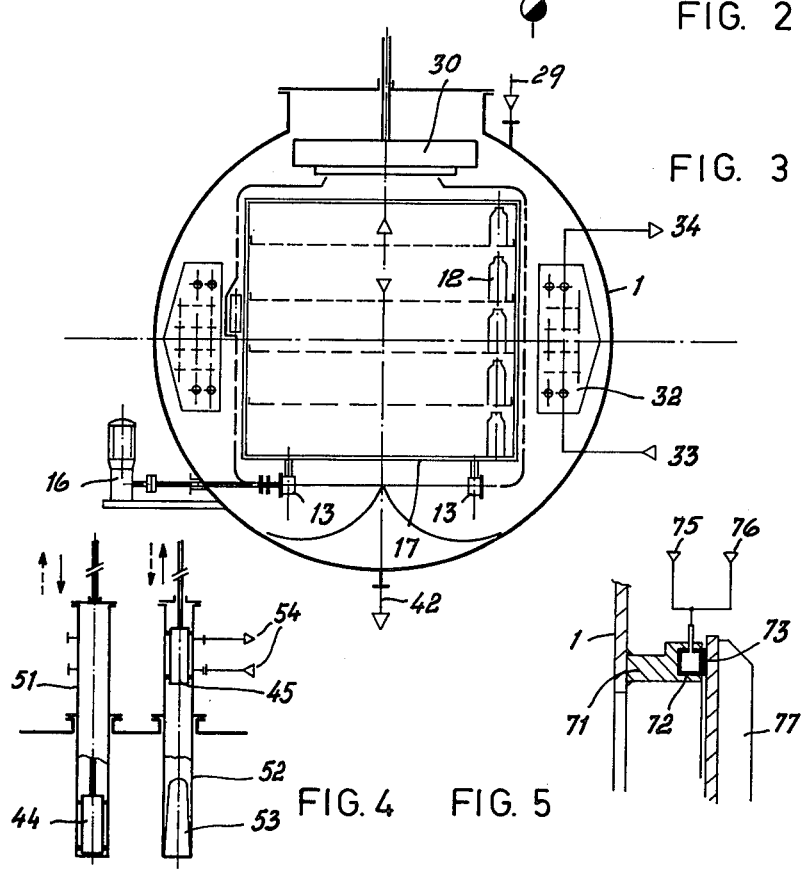
FIG. 3
FIG. 4  FIG. 5

STERILIZATION APPARATUS FOR INFUSION SOLUTIONS OR THE LIKE, FILLED IN CONTAINERS

BACKGROUND OF THE INVENTION

The invention relates to a sterilization installation for infusion solutions or the like which are filled in containers, in which installation the containers with the goods to be sterilized are exposed on shelves to a circulating, heated gaseous working medium and are subsequently cooled again by a circulating, indirectly cooled gaseous working medium. Sterilization installations of this type are described, for example, in the periodical "Die pharmazeutische industrie", 1975 (The pharmaceutical Industry); Heft (Vol.) 10, pages 825–829, Heft (Vol.) 11, pages 909–912, and Heft (Vol.) 12, pages 1071–1075. As working medium in such types of installations, one customarily uses either saturated steam, in given cases mixed with air, or circulating air is heated in the installation itself. When steam is used, and in particular during the cooling processes, a sudden pressure drop as a result of the condensation of the steam, and the danger of explosion of the hot containers associated therewith, have to be prevented through a correspondingly large supply of compressed air or of another gaseous protective medium. An improved apparatus of this type is described in a copending application by applicant, Ser. No. 890,202, filed on Apr. 20, 1978, having the same title, and assigned to the assignee of the present invention.

The increasing need for sterile infusion solutions or the like requires as economical an operation of the sterilization installations as possible. In cases of the known sterilization installations of the type here under discussion, the economics of operation are adversely affected thereby, namely in that the heating of the goods to be sterilized, the heat treatment at sterilization temperature, and the cooling of the goods to be sterilized after the heat treatment are all undertaken successively in a closed-off housing, which, together with its components, has to be heated and cooled again in each case.

A further problem, which has to be solved during the further development of the sterilization installations of the type here under discussion, is due to the demands made of the working conditions during the sterilization being more and more intensified, this being done in particular in view of the development of new highly sensitive infusion solutions or the like, and among other things, due to the need that the time between the preparation- and filling-operations of the solution to be sterilized, and the sterilization-process itself be shortened as much as possible. In the case of the known continuously operating sterilization installations, into which the containers filled with the sterilization goods can be introduced at once after the filling operations, a risk of a contamination of the solution exists, due to the use of a direct heat-exchange with heated or cooled water of the containers with the sterilization goods, for reasons which do not have to be explained here in detail; for this reason, the aforesaid demands can be met in cases of sterilization installations constructed for batch loading, the time intervals between the individual loading process being shortened.

SUMMARY OF THE INVENTION

The present invention has the aim of increasing the operational economics in the case of a sterilization installation of the initially mentioned type, through a better utilization of the expended quantity of heat and, at the same time, to achieve approximately a continuous operation by shortening the intervals between the individual batch loading processes.

This problem is solved, according to the present invention, by the housing of the sterilization installation enclosing three successive chambers which can be tightly closed by doors, preferably sliding doors, which chambers serve as a heating chamber, sterilization chamber and cooling chamber, respectively, and can be separately controlled with respect to the pressure-and temperature-conditions prevailing in them, so that the shelves with the sterilization goods can be passed one after the other through the chambers, and so that each chamber contains at least one fan for the circulation of its working medium; the first and the second chamber, moreover, contain devices for the supply of the heated working medium, and the last chamber contains at least one register for the indirect cooling of its working medium.

In the case of this installation, the housing walls and the components of the first and second chamber can be constantly maintained at high temperature, and the housing walls and the components of the third chamber can be kept at low temperature, so that in the first chamber in essence only the heat has to be supplied which is necessary for the heating of the sterilization goods to the sterilization temperature, and in the third chamber only the heat quantity has to be conducted away which is liberated during the re-cooling of the sterilization goods, whereas the heat supply to the second chamber is limited to the covering of the heat-losses which particularly occur when passing the shelves with the sterilization goods from the second chamber into the third chamber.

Since the entire treatment time of the sterilization goods is divided up into three dwelling times in different chambers, the dwelling time in each chamber, and consequently also that particular time-interval, is shortened to about one third, namely in that the first chamber after a loading may be again loaded with a new batch, so that an approximately continuous operation is achieved.

BRIEF DESCRIPTION OF THE DRAWING

Further characteristics and advantages of the invention will become apparent from the following description of an exemplified embodiment in conjunction with the drawings, in which:

FIG. 2 shows a cross-section through the second chamber, taken along the line II—II of FIG. 1;

FIG. 3 shows a cross-section through the third chamber, taken along the line III—III, of FIG. 1;

FIG. 4 shows a partial cross-section through a reference-container-arrangement, which serves for the control of the performance of the installation; and FIG. 5 shows a cross-section through a sealing arrangement for the sliding doors of the installation.

DESCRIPTION OF THE PREFERRED EMBODIMENTS

Figure 1:
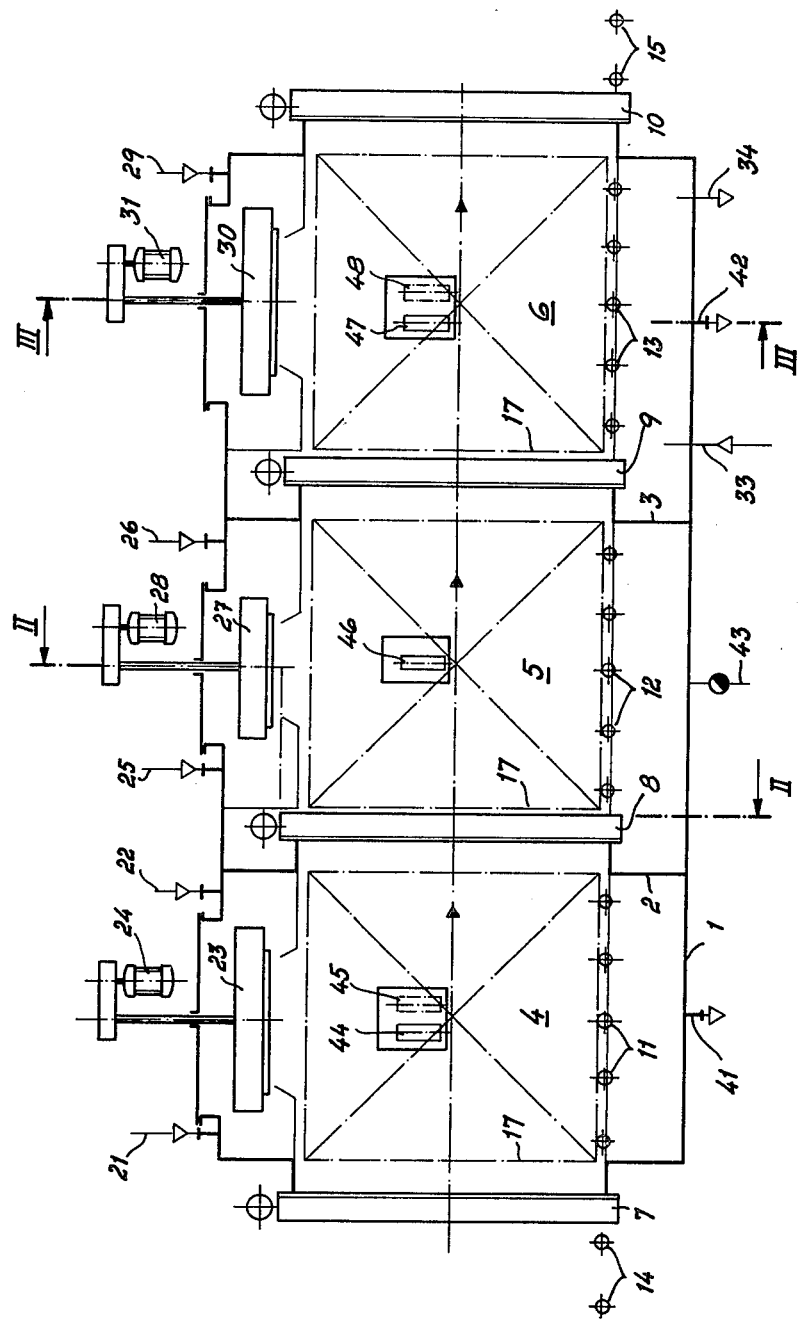
FIG. 1 shows a schematic longitudinal section through a sterilization installation, according to the present invention.

The sterilization installation which is illustrated in FIG. 1, with the omission of the foundation, includes an essentially cylindrical housing 1, which is subdivided by means of partitions 2 and 3, into three chambers, namely into a heating chamber 4, a sterilization chamber 5, and a cooling chamber 6. The first chamber 4 is accessible from the outside through a sliding door 7, and can be connected with the second chamber 5, by opening a sliding door 8, which chamber 5, on its part, can be connected with a third chamber 6, by opening a sliding door 9. The third chamber 6 can be closed-off with respect to the outside area by means of a sliding door 10. All sliding doors 7 to 10 are aligned with respect to one another, and a roll conveyor which consists of three roller units 11, 12, and 13, which are driven separately, extends from the inlet-door 7, to the outlet-door 10, of housing 1. This roll conveyor is supplemented with additional, driven roller units 14, or 15, located in front of, and behind the sterilization installation. The roller units are driven by means of the appropriately geared-down driving motors, of which one is indicated in FIG. 3, for the roller unit 13, and designed with 16. It is contemplated that programmable control means can be utilized to effect movement of the shelves between chambers.

Shelves 17, which are loaded with containers 18, containing material to be sterilized, (indicated only schematically in FIG. 1, but illustrated in more detail in FIG. 3) are individually inserted one after the other, by means of the roller units 11, and 14, through the inlet-door 7, into the heating chamber 4, and subsequently are passed along, one after the other, through the door 8, into the sterilization chamber 5, and further on through door 9, into the cooling chamber 6, in order to be finally discharged, by means of the roller unit 13, from the installation through the outlet door 10.

After introducing a shelf 17, loaded with containers to be sterilized, into the heating chamber 4, saturated steam is supplied via an inlet 21, into the heating chamber 4, in order to heat the sterilization goods at least approximately to the sterilization temperature; furthermore, through an additional inlet 22, compressed air is supplied, in order to protect the heated container from deformation or explosion, due to the increased pressure therein.

The working medium which heats the containers 18, and at the same time the protective pressure medium, are circulated in a known manner by means of a fan 23, which is driven by a motor 24, so that the working medium flows through the open compartments of shelf 17, and uniformly heats the containers 18, containing the sterilization goods.

After attaining the sterilization temperature, the shelf 17 is passed into the previously emptied sterilization chamber 5. Via inlets 25, and 26, saturated steam and compressed air as well, are introduced into the chamber 5, and this mixture is again circulated by means of a fan 27, driven by a motor 28. The sterilization goods remain in the chamber 5 for the required sterilization time.

After this sterilization time has elapsed, the shelf 17 is passed on further into the cooling chamber 6. Prior to this, compressed air has already been introduced through the inlet 29 into this chamber 6, in order to create the required protective-pressure for the containers 18, with the material to be sterilized. The compressed air is then circulated by means of a fan 30, which is driven by a motor 31, and the compressed air thus passes through a cooling register 32 (FIG. 3) which is arranged in the chamber 6. The cooling register 32 is supplied with cooling water via the inlet- and outlet lines 33, and 34. After attaining the desired heat exchange, the corresponding shelf 17 is discharged from the installation through the outlet door 10.

The temperature control in the first chamber 4, and the second chamber 5, takes place substantially through the adjustment of the steam supply, whereas the pressure in the chambers 4 and 5 is regulated through appropriate supply of compressed air. In the third chamber 6, the temperature control is carried out by adjusting the supply of cooling water, and the pressure control is carried out by regulating the supply of compressed air.

After the first chamber 4 is emptied, and prior to the introduction of a fresh shelf 17, loaded with the sterilization goods, the pressure in the chamber 4 has to be reduced to atmospheric pressure and, for this purpose, the first chamber 4 can be made to communicate with the atmosphere by means of an outlet 41. After the introduction of the fresh shelf 17, into the first chamber 4, the pressure in the containers 18 increases due to the heating processes, and the protective-pressure has to be increased accordingly. When passing the shelf 17 into the second chamber 5, the pressure-and temperature-conditions remain substantially unchanged. Prior to passing the shelf 17 into the third chamber 6, the required protective-pressure has to be built-up in the chamber 6, as mentioned above, and before the shelf 17 leaves the chamber 6, the protective-pressure in the chamber has to be reduced, for which purpose an outlet 42 is provided in this chamber.

The outlets 41, and 42, in the first chamber 4, and in the third chamber 6, as well as an additional outlet 43, in the second chamber 5, serve for the purpose of discharging the condensate.

For the control of the pressure- and temperature-conditions in the individual chambers, at least one reference container is assigned to each chamber, the contents of which—in a manner known per se, and, for example, described in the referenced "Background of the Invention" section,-simulate the pressure- and temperature-conditions in the interior of the container containing the actual sterilization goods. In these reference containers, pressure- and temperature- sensing elements are arranged, which control devices for the regulation of pressure and temperature in the corresponding chamber as a function of the pressure- and temperature-values measured in the reference container.

If the first and third chamber, respectively, only one reference container is provided, then a device for the forced cooling of the first chamber's reference-container to the temperature of the atmosphere has to be provided, and a device for the forced heating of the third chamber's reference-container to the temperature in the second chamber, after emptying of the first or third chamber, has to be provided, so that each reference-container, in the shortest possible time after introduction of the next shelf into a corresponding chamber, can simulate the pressure- and temperature-conditions which prevail in the sterilization-material container introduced with the shelf.

In the case of the illustrated preferred exemplified embodiment, two movable reference-containers 44, 45, are arranged in the first chamber 4; in the second chamber 5, a stationary reference-container 46 is arranged, and in the third chamber 6, again two movable reference-containers 47, 48, are arranged. The two reference-containers in the first and in the third chamber are made to be alternately operative, one of them in each case being exposed to the temperature prevailing in the interior of the chamber, and the other being exposed to a lower or higher temperature. This can be achieved in the case of the first chamber 4, e.g., according to FIG. 4, namely in that in the housing 1, two separate guide-members 51, 52, are provided for the two reference-containers 44, and 45, which guide-members 51, 52, make it possible to move one reference container in each case from a zone in the interior of the chamber—in which it is exposed to the working medium of the chamber 4, namely through the openings 53, in the otherwise closed system (see reference-container 44, in FIG. 4)—into a cooling zone outside of the chamber, in which zone the corresponding reference-container can be cooled down by means of a cooling liquid circulation system 54 to the temperature of the external atmosphere (see reference-container 44 in FIG. 4), and in that one simultaneously moves the other reference-container in the opposite sense.

In an analogous manner, the reference-containers 47, 48, of the third chamber 6, can likewise be movably arranged in this manner, and can be connected with one another in a manner allowing displacement in the opposite sense, so that in each case one container is cooled in the interior of the chamber together with the containers for the sterilization goods, whereas the other container is heated outside of the chamber to the temperature at which the sterilization goods of the next batch are passed into the chamber 6.

As it can be seen from FIG. 2, the housing 1—in the area of the inner sliding doors 8, and 9—has a sealingly mounted compartment 61, which receives a door-closing member of a door 8 (best seen in FIG. 5) which is preferably hung by means of rollers 62, on a rail 63 during the opening of the door by means of an actuation cylinder 64.

The sealing, at least of the door 8, between the first and the second chamber, as well as of the door 9, between the second and the third chambers, is carried out advantageously according to FIG. 5, along a flange 71, of the compartment of the housing 1, this being done by means of a hose 73, which is inserted into a groove 72, of the flange 71, so that the hose 73 can be inflated by independent respective pressure means, and comes to lie in a sealing manner against the closing member 77.

According to FIG. 5, by way of example, steam can be introduced through a first inlet 75, and compressed air can be introduced through the second inlet 76, into the sealing-hose 73, through which action it is ensured that a trouble-free seal results, even if a compressed air or compressed fluid source is out of action.

It should still be mentioned that for the attaining of as uniform a heating as possible of all containers filled with the sterilization goods, in a further advantageous development outlined in the referenced application Ser. No. 890,202, a control or regulating-device can be provided, in at least the first chamber and the third chamber, by means of which the circulating working medium can be conducted through the shelf supporting the sterilization-material container in cyclic succession, or in each case simultaneously, and in different directions.

Furthermore, the operation of the installation is advantageously program-controlled in such a manner that the transfer of the shelves from the first chamber into the second chamber takes place in each case immediately after the containers attain the sterilization temperature, the transfer from the second chamber into the third chamber takes place in each case immediately after expiration of the prescribed sterilization time, and the transfer from the third chamber into the atmosphere takes place in each case immediately after the containers attain the desired cooling temperature; this is done in order to keep the sterilization goods at high tenperatures only during the time absolutely required for the sterilization, and in order to free the individual chambers as quickly as possible for the next batch to be processed.

I wish it to be understood that I do not desire to be limited to the exact details of construction shown and described, for obvious modifications will occur to a person skilled in the art.

Having thus described the invention, what I claim as new and desire to be secured by Letters Patent is as follows:

1. A sterilization device adopted for processing in a substantially contamination-free manner a plurality of containers disposed on support means therefor, said containers being filled with goods to be sterilized, comprising in combination:
   a housing provided with a passage for receiving and discharging said support means,
   preheating means for preheating said containers to a predetermined temperature within said housing, and including first supply means adapted to supply a heated fluid to said preheating means,
   heating means for at least maintaining said containers at said predetermined temperature within said housing, including second supply means adapted to supply said heated fluid to said heating means, so that said containers and the goods therein become sterilized,
   cooling means disposed in said housing and adapted to use a cooled and circulating fluid for cooling said containers to a second predetermined temperature following sterilization of said containers by said heating means,
   a plurality of openable and closeable doors arranged in said passage to define first, second and third chambers encompassing said preheating means, said heating means, and said cooling means, respectively, including means for separately controlling each of said chambers with respect to temperature and pressure prevailing therein, and means for passing said containers sequentially through said chambers, corresponding of said chambers substantially remaining intermittently closed, when said containers are being processed therein, and
   agitating means provided in each of said chambers for circulating the fluid contained in the respective chamber therethrough.

2. An installation as defined in claim 1, wherein said first chamber and said third chamber each have a controllable outlet to the atmosphere.

3. An installation according to claim 1, wherein pneumatic sealing means are provided at least for the door between the first chamber and the second chamber, and for the door between the second chamber and the third chamber, said pneumatic sealing means being operable by mutually independent pressure media, respectively.

4. An installation according to claim 1, further including a programmable control device for effecting the transfer of the shelves from the first chamber into the second chamber immediately after the containers attain the sterilization temperature, for effecting transfer from the second chamber into the third chamber immediately after expiration of the prescribed sterilization time, and for effecting transfer from the third chamber to the atmosphere immediately after the containers attain the desired cooling temperature.

5. An installation as defined in claim 1, wherein means for passing said containers through said chambers includes drivable rollers within said passage for forwarding said support means through said chambers.

6. A sterilization device as defined in claim 5, wherein said support means are shelves, wherein said first chamber is provided with an inlet for said heating fluid, and said second and third chambers are each provided with an inlet for a protective fluid, and wherein said agitating means includes a fan being provided in each chamber for whirling said fluid through said shelves.

7. An installation as claimed in claim 1, wherein at least said first chamber and said third chamber are provided with means for controlling the flow of said fluids through said support means.

8. An installation as claimed in claim 7, wherein said flow control means periodically direct said fluids through different parts of said support means.

9. An installation as defined in claim 7, wherein said flow control means divert said fluid simultaneously in different directions.

10. An installation as defined in claim 1, wherein at least one reference container is arranged in each chamber to simulate pressure- and temperature-conditions in the containers to be sterilized, said reference containers cooperating with external control devices adapted to regulate pressure- and temperature-conditions in respective chambers in response to reference signals received from said containers.

11. An installation as defined in claim 10, wherein said first chamber includes means for cooling the reference container disposed therein to the temperature of the atmosphere, and said third chamber includes means for heating the reference container disposed therein to the temperature of said second chamber.

12. An installation as defined in claim 10, wherein said first chamber and said third chamber include, respectively, at least two alternately operating reference containers, one of said alternately operating containers being exposed to conditions in its assigned chamber while the other of said alternately operating containers is maintained near room temperature and pressure conditions.

13. An installation as defined in claim 12, wherein said alternately operating reference containers are movably arranged in their respective chambers and are coupled together for relative movement in such a manner, that while one container is introduced into its assigned chamber, the other of the alternately operating reference containers is moved out of its assigned chamber.

* * * * *